(12) United States Patent
Grasman et al.

(10) Patent No.: US 9,364,546 B2
(45) Date of Patent: Jun. 14, 2016

(54) MELT-EXTRUDED COMPOSITION COMPRISING A CELLULOSE ETHER

(71) Applicant: Dow Global Technologies LLC, Midland, MI (US)

(72) Inventors: Nicholas S. Grasman, Midland, MI (US); True L. Rogers, Midland, MI (US); Oliver Petermann, Hamburg (DE); Meinolf Brackhagen, Walsrode (DE); Roland Adden, Walsrode (DE)

(73) Assignee: Dow Global Technologies LLC

( * ) Notice: Subject to any disclaimer, the term of this patent is extended or adjusted under 35 U.S.C. 154(b) by 42 days.

(21) Appl. No.: 14/389,838

(22) PCT Filed: Apr. 8, 2013

(86) PCT No.: PCT/US2013/035594
§ 371 (c)(1),
(2) Date: Oct. 1, 2014

(87) PCT Pub. No.: WO2013/154981
PCT Pub. Date: Oct. 17, 2013

(65) Prior Publication Data
US 2015/0057356 A1  Feb. 26, 2015

Related U.S. Application Data

(60) Provisional application No. 61/622,760, filed on Apr. 11, 2012.

(51) Int. Cl.
*A61K 9/14* (2006.01)
*A61K 47/38* (2006.01)
*C08B 11/193* (2006.01)
*C08L 1/28* (2006.01)
*A61K 9/16* (2006.01)
*A61K 9/20* (2006.01)
*A61K 31/192* (2006.01)
*B29C 47/00* (2006.01)
*B29K 1/00* (2006.01)
*B29K 105/00* (2006.01)

(52) U.S. Cl.
CPC .............. *A61K 47/38* (2013.01); *A61K 9/1652* (2013.01); *A61K 9/2095* (2013.01); *A61K 31/192* (2013.01); *B29C 47/004* (2013.01); *B29C 47/0066* (2013.01); *C08B 11/193* (2013.01); *C08L 1/28* (2013.01); *C08L 1/284* (2013.01); *B29C 2793/009* (2013.01); *B29K 2001/08* (2013.01); *B29K 2105/0035* (2013.01)

(58) Field of Classification Search
CPC ..................................................... A61K 47/38
See application file for complete search history.

(56) References Cited

U.S. PATENT DOCUMENTS 4,001,211 A  1/1977  Sarkar

FOREIGN PATENT DOCUMENTS

| EP | 0872233 A1 | 10/1998 |
|---|---|---|
| WO | 0122938 A1 | 4/2001 |
| WO | 2005115330 A2 | 12/2005 |
| WO | 2006121941 A2 | 11/2006 |
| WO | 2008050209 A1 | 5/2008 |
| WO | 2011119287 A1 | 9/2011 |
| WO | 2011119289 A2 | 9/2011 |
| WO | 2012051034 A1 | 4/2012 |
| WO | 2012051035 A1 | 4/2012 |

OTHER PUBLICATIONS

Drug Disc. Today, vol. xxx, No. xx, 2011, The use of amorphous solid dispersions, van den Mooter.
J. of Drug Targeting, 18(10), 2010, p. 704-731, Using polymeric precipitation inhibitors to improve the absorption of poorly water-soluble drugs, Warren et al.
Int. J. of Pharm., 212, 2001, p. 213-221, Crystallization of hydrocortisone acetate, Raghavan et al.
Int. J. of Pharm., 251, 2003, p. 165-174, Characterization of solid dispersions of itraconazole and hydroxypropylmethylcellulose prepared by melt-extrusion, Verreck et al.
Europ. J. of Pharma & Bio., 54, 2002, p. 107-117, Melt extrusion: from process to drug delivery technology, Breitenbach.

*Primary Examiner* — Paul Dickinson

(57) ABSTRACT

A melt-extruded polymer composition comprising a) at least one cellulose ether, b) one or more active ingredients and c) one or more optional additives, wherein said at least one cellulose ether has an MS (hydroxyalkyl) of 0.05 to 0.55 and hydroxyl groups of anhydroglucose units are substituted with methyl groups such that [s23/s26−0.2*MS(hydroxyalkyl)] is 0.32 or less, wherein s23 is the molar fraction of anhydroglucose units wherein only the two hydroxyl groups in the 2- and 3-positions of the anhydroglucose unit are substituted with a methyl group and wherein s26 is the molar fraction of anhydroglucose units wherein only the two hydroxyl groups in the 2- and 6-positions of the anhydroglucose unit are substituted with a methyl group.

16 Claims, No Drawings

MELT-EXTRUDED COMPOSITION COMPRISING A CELLULOSE ETHER

FIELD OF THE INVENTION

This invention relates to melt-extruded compositions comprising a cellulose ether and to a process for producing them.

INTRODUCTION

A large number of presently known drugs have a low solubility in water, so that complex techniques are required to prepare a dosage form. Much research is spent on the use of pharmaceutically acceptable water-soluble polymers in combination with drugs of low water solubility. The use of water-soluble polymers aims at reducing the crystallinity of the drug, thereby minimizing the activation energy necessary for the dissolution of the drug, as well as establishing hydrophilic conditions around the drug molecules, thereby improving the solubility of the drug itself to increase its bioavailability, i.e., its in vivo absorption by an individual upon ingestion. However, simple blending of a water-soluble polymer with a drug of low water solubility generally does not reduce the crystallinity of the drug.

G. Van den Mooter, "The use of amorphous solid dispersions: A formulation strategy to overcome poor solubility and dissolution rate", Drug Discov Today: Technol (2011), doi:10.1016/j.ddtec.2011.10.002, discusses the preparation of amorphous solid dispersions to increase the bioavailability of poorly soluble drugs by improving their rate and extent of dissolution. The two most applied manufacturing methods for preparing amorphous solid dispersions are said to be spray drying and hot melt extrusion. The former process starts from a solution of the drug and a carrier in a common organic solvent or mixture of solvents. This solution is atomized using a nozzle and the solvent is subsequently quickly evaporated (order of magnitude is milliseconds). The very fast solvent evaporation contributes to the amorphous state of the solid dispersion.

Dallas B. Warren et al. (Journal of Drug Targeting, 2010; 18(10): 704–731) have studied the use of water-soluble cellulose ethers as polymeric precipitation inhibitors, such carboxymethyl cellulose (CMC), methyl cellulose (MC), hydroxyethyl cellulose (HEC), and hydroxypropylmethyl cellulose (HPMC) to improve the absorption of poorly water-soluble drugs.

S. L. Raghavan et al. (International Journal of Pharmaceutics 212 (2001) 213–221), have studied the influence of hydroxypropyl methylcellulose (HPMC), methylcellulose (MC), polyvinyl pyrrolidone (PVP) and polyethylene glycol (PEG400) on the crystallization of hydrocortisone acetate (HA).

Alternatively, solid dispersions are produced by hot melt extrusion. In the most common setup a powder blend is introduced via a hopper into a heated barrel with a rotating screw, where the powder blend is intensively mixed in the softened or partially or completely melted state and moved towards a die that shapes the melt as strands, films, pellets, tablets or capsules. The amount of heat and shear forces applied, as well as the rate of cooling when the extrudate leaves the die contributes to the physical structure of the solid dispersion. Films are particularly useful for persons who have difficulty swallowing tablets. An amorphous solid dispersion is produced when the drug is present in a substantially amorphous, non-crystalline state and is stable in this state at room temperature and pressure for an extended period of time.

WO2011/119287 discloses a mono-layer or multi-layer film wherein at least one of the layers has a thickness of at least 0.125 mm and is produced from a melt-extruded polymer composition of a) a water-soluble polymer, b) an active ingredient and c) an adjuvant selected from mono- and disaccharides, sugar alcohols, low molecular weight water soluble polymers, and salts of cross-linked carboxymethylcellulose. Polyethylene oxides and a hydroxypropyl methylcellulose plastizised with propylene glycol are disclosed in the examples.

WO2011/119289A2 discloses a process for producing a melt-extruded film which comprises the steps of blending a) a water-soluble polymer, b) an active ingredient, and c) optional additives and subjecting the blend to melt-extrusion to produce an extruded melt and drawing the extruded melt at a draw-down ratio of from 1.5 to 20 to a film of a thickness of at least 0.04 mm Polyethylene oxide is disclosed in the examples.

European Patent Application EP 0 872 233 discloses a solid dispersion comprising (a) loviride and (b) one or more pharmaceutically acceptable water-soluble polymers. The solid dispersion is produced by melt-extrusion wherein the components (a) and (b) and optional additives are blended, the blend is heated to obtain a homogeneous melt, the obtained melt is forced through one or more nozzles and the melt is cooled till it solidifies. The solid dispersion product is milled or ground to particles. The particles are formulated into tablets or capsules. Among the large variety of listed water-soluble polymers hydroxypropyl methyl cellulose (HPMC) is said to be preferred, particularly HPMC 2910 which comprises about 29 weight percent of methoxyl groups and about 10 weight percent of hydroxypropoxyl groups.

Geert Verreck et al., "Characterization of solid dispersions of itraconazole and hydroxypropylmethylcellulose prepared by melt extrusion, part I", International Journal of Pharmaceutics 251 (2003), p. 165–174, discloses that a milled melt extrudate formulation of 40 weight percent of itraconazole and 60 weight percent of HPMC is chemically and physically stable for periods in excess of 6 months as indicated by the absence of degradation products or re-crystallization of the drug.

However, commercially available hydroxypropyl methylcelluloses often do not readily form solid amorphous dispersions with active ingredients and are known to have narrow thermal processing windows. The thermal processing window is defined as the temperature region in which the polymer is in a relaxed state but has not yet begun thermal decomposition. For most known hydroxypropyl methylcelluloses the temperature at which the polymer transitions from a rigid to a relaxed state (glass transition temperature $T_g$) is in excess of 150° C., while the decomposition temperature is as low as 250° C.

Accordingly, it would be desirable to find new melt-extruded compositions comprising a cellulose ether. It would be particularly desirable to find new compositions comprising a cellulose ether which can form a solid dispersion, preferably a solid amorphous dispersion, with active ingredients and be melt-extruded in a reasonably broad processing window.

SUMMARY OF THE INVENTION

Surprisingly, it has been found that melt-extrusion and the production of solid dispersions of polymer compositions comprising a cellulose ether and an active ingredient is facilitated if the polymer composition to be melt-extruded comprises at least one cellulose ether wherein the ether substituents have a specific distribution pattern.

One aspect of the present invention is a melt-extruded polymer composition which comprises a) at least one cellulose ether, b) one or more active ingredients and c) one or more optional additives, wherein said at least one cellulose ether has anhydroglucose units joined by 1-4 linkages and has methyl groups, hydroxyalkyl groups, and optionally alkyl groups being different from methyl as substituents such that said at least one cellulose ether has an MS (hydroxyalkyl) of 0.05 to 0.55,
and
hydroxyl groups of anhydroglucose units are substituted with methyl groups such that [s23/s26−0.2*MS(hydroxyalkyl)] is 0.32 or less,
wherein s23 is the molar fraction of anhydroglucose units wherein only the two hydroxyl groups in the 2- and 3-positions of the anhydroglucose unit are substituted with a methyl group and
wherein s26 is the molar fraction of anhydroglucose units wherein only the two hydroxyl groups in the 2- and 6-positions of the anhydroglucose unit are substituted with a methyl group.

Another aspect of the present invention is a process for producing a melt-extruded polymer composition which comprises the steps of
i) blending a) at least one cellulose ether, b) one or more active ingredients and c) one or more optional additives, and
ii) subjecting the blend to melt-extrusion,
wherein said at least one cellulose ether is as defined above.

Yet another aspect of the present invention is the use of at least one cellulose ether as defined above for producing a melt-extruded polymer composition.

DETAILED DESCRIPTION OF THE INVENTION

The melt-extruded polymer composition comprises a) at least one cellulose ether which has anhydroglucose units joined by 1-4 linkages and which has methyl groups, hydroxyalkyl groups, and optionally alkyl groups being different from methyl as substituents. The hydroxyalkyl groups can be the same or different from each other. Preferably the cellulose ether comprises one or two kinds of hydroxyalkyl groups, more preferably one or more kinds of hydroxy-$C_{1-3}$-alkyl groups, such as hydroxypropyl and/or hydroxyethyl. Useful optional alkyl groups are, e.g., ethyl or propyl, ethyl being preferred.

Preferred ternary cellulose ethers are ethyl hydroxypropyl methyl celluloses, ethyl hydroxyethyl methyl celluloses, or hydroxyethyl hydroxypropyl methyl celluloses. Preferred cellulose ethers are hydroxyalkyl methyl celluloses, particularly hydroxy-$C_{1-3}$-alkyl methyl celluloses, such as hydroxypropyl methylcelluloses or hydroxyethyl methylcelluloses.

An essential feature of the cellulose ether is its unique distribution of methyl groups on the anhydroglucose units such that [s23/s26−0.2*MS(hydroxyalkyl)] is 0.32 or less, preferably 0.30 or less, more preferably 0.28 or less, and most preferably 0.25 or less, 0.23 or less, or 0.21 or less. Typically [s23/s26−0.2*MS(hydroxyalkyl)] is 0.07 or more, more typically 0.10 or more, and most typically 0.13 or more. As used herein, the symbol "*" represents the multiplication operator.

In the ratio s23/s26, s23 is the molar fraction of anhydroglucose units wherein only the two hydroxyl groups in the 2- and 3-positions of the anhydroglucose unit are substituted with methyl groups and s26 is the molar fraction of anhydroglucose units wherein only the two hydroxyl groups in the 2- and 6-positions of the anhydroglucose unit are substituted with methyl groups. For determining the s23, the term "the molar fraction of anhydroglucose units wherein only the two hydroxyl groups in the 2- and 3-positions of the anhydroglucose unit are substituted with methyl groups" means that the 6-positions are not substituted with methyl; for example, they can be unsubstituted hydroxyl groups or they can be substituted with hydroxyalkyl groups, methylated hydroxyalkyl groups, alkyl groups different from methyl or alkylated hydroxyalkyl groups. For determining the s26, the term "the molar fraction of anhydroglucose units wherein only the two hydroxyl groups in the 2- and 6-positions of the anhydroglucose unit are substituted with methyl groups" means that the 3-positions are not substituted with methyl; for example, they can be unsubstituted hydroxyl groups or they can be substituted with hydroxyalkyl groups, methylated hydroxyalkyl groups, alkyl groups different from methyl or alkylated hydroxyalkyl groups.

The term "hydroxyl group substituted with methyl group" or "hydroxyl group substituted with hydroxyalkyl group" as used herein means that the hydrogen atom on the hydroxyl group is replaced by a methyl group or a hydroxyalkyl group.

Formula I below illustrates the numbering of the hydroxyl groups in anhydroglucose units. Formula I is only used for illustrative purposes and does not represent the cellulose ethers of the invention; the substitution with hydroxyalkyl groups is not shown in Formula I.

Formula I

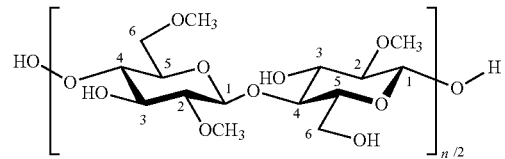

The cellulose ether preferably has a DS(methyl) of from 1.0 to 2.5, more preferably from 1.1 to 2.4, most preferably from 1.2 to 2.2, and particularly from 1.6 to 2.2. The degree of the methyl substitution, DS(methyl), of a cellulose ether is the average number of OH groups substituted with methyl groups per anhydroglucose unit. For determining the DS(methyl), the term "OH groups substituted with methyl groups" does not only include the methylated OH groups directly bound to the carbon atoms of the cellulose backbone but also methylated OH groups that have been formed after hydroxyalkylation.

The cellulose ether has an MS(hydroxyalkyl) of 0.05 to 0.55, preferably 0.07 to 0.50, more preferably 0.10 to 0.45, most preferably 0.15 to 0.35. The degree of the hydroxyalkyl substitution is described by the MS (molar substitution). The MS(hydroxyalkyl) is the average number of hydroxyalkyl groups which are bound by an ether bond per mole of anhydroglucose unit. During the hydroxyalkylation, multiple substitutions can result in side chains.

The sum of the MS(hydroxyalkyl) and the DS(methyl) preferably is at least 1.8, more preferably at least 1.9, most preferable up to 2.0 and preferably up to 2.7, more preferably up to 2.5.

The determination of the % methoxyl and % hydroxypropoxyl in hydroxypropyl methylcellulose is carried out according to the United States Pharmacopeia (USP 32). The values obtained are % methoxyl and % hydroxypropoxyl. These are subsequently converted into degree of substitution (DS) for methyl substituents and molar substitution (MS) for hydroxypropyl substituents. Residual amounts of salt have been taken into account in the conversion.

The viscosity of the cellulose ether incorporated in the melt-extruded polymer composition of the present invention can be in a wide range. Typically it is in a range from 2.4 to 200,000 mPa·s. Preferred viscosities are from 2.4 to 100 mPa·s, more preferably from 2.5 to 50 mPa·s, and most preferably from 3 to 30 mPa·s, measured as a 2 weight-% aqueous solution at 20° C. according to ASTM D2363-79 (Reapproved 2006).

Surprisingly, it has been found that melt-extruded compositions comprising the above-described cellulose ethers which have an [s23/s26−0.2*MS(hydroxyalkyl)] of 0.32 or less are better able to form and maintain substantially amorphous solid dispersions with active ingredients, as compared to cellulose ethers which have a comparable DS(methyl) and MS(hydroyxyalkyl) and a comparable viscosity, but which have an [s23/s26-0.2*MS(hydroxyalkyl)] of more than 0.32.

Methods of making the above described cellulose ethers are described in detail in the Examples. Some aspects of the process for making the cellulose ethers are described in more general terms below.

The cellulose ether described above can be obtained by a multistage etherification process comprising:
a first stage comprising:
i. treating cellulose pulp with a first amount of alkalizing agent, and
ii. addition of at least one methylating agent to the cellulose pulp, subsequent heating of the reaction mixture to a reaction temperature of 70° C. or more and thereafter
at least one additional stage comprising:
iii. addition of an additional amount of alkalizing agent to the reaction mixture at a rate of less than 0.04 molar equivalents of alkalizing agent per mole of anhydroglucose units per minute, and, optionally for each individual additional stage,
iv. addition of an additional amount of at least one methylating agent to the reaction mixture,
wherein before, after or concurrently with the addition of the alkalizing agent in the first stage at least one hydroxyalkylating agent, and optionally at least one alkylation agent different from a methylating agent, is added to the cellulose pulp, or, as the etherification of the cellulose pulp proceeds, to the partially reacted cellulose pulp.

The cellulose raw material for preparing the cellulose ether is typically cellulose pulp obtained from cotton or wood, preferably wood pulp. It is typically provided in powder or chip form.

In the above-mentioned process the cellulose pulp or, as the reaction of cellulose pulp to the hydroxyalkyl methyl cellulose proceeds, the partially reacted cellulose pulp, is alkalized in two or more stages, preferably in two or three stages, in one or more reactors with an alkalizing agent. The alkalizing agent may be any strong base such as an alkali metal hydroxide, preferably sodium hydroxide, caustic soda or lime or a mixture of more than one of such strong bases, employed as an aqueous solution. Usually an aqueous solution of an alkali metal hydroxide is employed, preferably having an alkali metal hydroxide content of from 30 to 70 percent, more preferably from 35 to 60 percent, most preferably from 48 to 52 percent, based on the total weight of the aqueous solution of the alkali metal hydroxide.

In one embodiment, an organic solvent such as dimethyl ether is added to the reactor as a diluent and a coolant. Likewise, the headspace of the reactor is optionally purged with an inert gas (such as nitrogen) to control oxygen-catalyzed depolymerization of the cellulose ether product.

In the first stage of the process the cellulose pulp is treated with a first amount of alkalizing agent, typically from 1.2 to 3.5 molar equivalents of alkalizing agent per mole of anhydroglucose units in the cellulose. The treatment can be conducted by any means known in the art such as by steeping in a bath or stirred tank or spraying. Uniform swelling and distribution of the alkalizing agent in the pulp may be achieved by mixing and agitation. In the first stage the rate of addition of the aqueous solution of the alkalizing agent to the cellulose pulp is not critical. It may be added in several portions, e.g. 2 to 4 portions, or continuously. During first stage alkalization, which usually lasts from 15 to 60 minutes, the temperature is typically maintained at 45° C. or below.

Moreover, a methylating agent such as methyl chloride or dimethyl sulfate is added to the cellulose pulp within the first stage of the process, before, after or concurrently with the first amount of alkalizing agent, preferably after the addition of the alkalizing agent. The methylating agent can be added to the cellulose or, as the reaction of cellulose pulp to the hydroxyalkyl methyl cellulose proceeds, to partially reacted cellulose pulp, in a single stage, but it is preferably added in two or more stages, more preferably two or three stages, most preferably two stages.

If the methylating agent is added in a single stage, it is generally added in an amount of from 3.5 to 6.0 mole of methylating agent per mole of anhydroglucose units, but in any event it is added in at least an equimolar amount, compared to the alkalizing agent added in the first stage, before heating the reaction mixture. If the methylating agent is added in a single stage, it is preferably added at a rate of from 0.25 to 1.0 molar equivalents of methylating agent per mole of anhydroglucose units per minute. The methylating agent used in the first stage may be pre-mixed with any conventional suspending agent. In this case, a mixture comprising from 20 to 50%, more preferably from 30 to 50%, of the suspending agent, based on the total weight of the suspending agent and the at least one methylating agent is preferably employed.

Once the cellulose has been treated with the first amount of alkalizing agent and the additions of the methylating agent and possible further components of the first stage, preferably conducted also at a temperature of 45° C. or below, have been accomplished, the reaction mixture is heated, typically within 30 to 80 minutes, to a reaction temperature of at least 70° C., preferably in the range of 70–90° C., more preferably in the range of 70–80° C. Usually the reaction is then allowed to proceed at this reaction temperature for 10 to 30 minutes.

Subsequently the process comprises at least one additional stage comprising addition of an additional amount of alkalizing agent and, optionally for each individual additional stage, addition of an additional amount of the methylating agent to the reaction mixture. The total amount of additional alkalizing agent added as aqueous solution within the at least one additional stage typically ranges from 1.0 to 2.9 molar equivalents of alkalizing agent per mole of anhydroglucose units. Preferably, the molar equivalent ratio between the amount of alkalizing agent added in the first stage and the amount of alkalizing agent added in total in the at least one additional stage is from 0.6:1 to 3.5:1. It is important to add the alkalizing agent in the at least one additional stage slowly to the reaction mixture, i.e. at a rate of less than 0.04, preferably less than 0.035, more preferably less than 0.03 molar equivalents of alkalizing agent per mole of anhydroglucose units per minute. The alkalizing agent of the second stage is generally added at a temperature of from 55 to 85° C., preferably from 60 to 80° C.

Typically the methylating agent is used in a total amount in the range of 2 to 6 moles per mole of anhydroglucose units. If the methylating agent is added not only in the first stage, but also in at least one additional subsequent stage, preferably in one additional stage, it is typically added in an amount of 2.0 to 4.0 mole of methylating agent per mole of anhydroglucose units in the first stage and in a total amount of 1.5 to 3.4 mole of methylating agent per mole of anhydroglucose units in the at least one additional stages. In any event the methylating agent is added in at least an equimolar amount, compared to the alkalizing agent present in the reaction mixture. Accordingly, the methylating agent of the second stage, if any, is added to the reaction mixture before or during the second and optionally third stage of adding the alkalizing agent in such a manner that the cellulose or, as the reaction of cellulose pulp to the hydroxyalkyl methyl cellulose proceeds, the partially reacted cellulose pulp, is continuously contacted with an at least equimolar equivalent amount of the methylating agent compared to the alkalizing agent.

If the methylating agent is added in two stages, the methylating agent of the first stage is preferably added at a rate of from 0.25 to 0.5 molar equivalents of methylating agent per mole of anhydroglucose units per minute. The methylating agent of the single stage or of the first stage may be pre-mixed with a suspending agent. In this case the mixture of suspending agent and methylating agent preferably comprises from 20 to 50 weight percent, more preferably from 30 to 50 weight percent, of the suspending agent, based on the total weight of methylating agent and suspending agent.

If the methylating agent is added in two stages, the second stage of methylating agent is generally added to the reaction mixture after having heated the reaction mixture to a temperature of about 70-90° C. for 10 to 30 minutes. The methylating agent of the second stage is preferably added at a rate of from 0.25 to 0.5 molar equivalents of methylating agent per mole of anhydroglucose units per minute. If the methylating agent is added in two stages, the molar ratio between the methylating agent of the first stage and the methylating agent of the second stage is generally from 0.68:1 to 1.33:1. The methylating agent in each of the at least one additional stage, if used therein, should be added to the reaction mixture prior to or during the addition of the additional amount of alkalizing agent of that stage in such a manner that the cellulose is continuously contacted with an at least equimolar equivalent amount of the at least one methylating agent compared to the alkalizing agent.

As an alternative to the procedure described above wherein the methylating agent and alkalizing agent each are added in two stages, the methylating agent of the second stage may be added to the reaction mixture after a portion of the alkalizing agent of the second stage has been added, followed by subsequent addition of alkalizing agent; i.e., the methylating agent is added in a second stage, which is followed by the addition of a third stage alkalizing agent. In this embodiment of the process, the total amount of alkalizing agent per mole of anhydroglucose added in the second and third stage is generally 1.0 to 2.9 moles per mole of anhydroglucose units, of which preferably 40 to 60 percent are added in the second stage and 60 to 40 percent are added in the third stage. Preferably the alkalizing agent used in the third stage is added slowly, i.e., at a rate of less than 0.04, typically at a rate of less than 0.03 molar equivalents of alkalizing agent per mole of anhydroglucose units per minute. The methylating agent and alkalizing agent of the third stage are generally added at a temperature of from 55 to 85° C., preferably from 60 to 80° C.

One or more, preferably one or two, hydroxyalkylating agents, such as ethylene oxide and/or propylene oxide are also added to the cellulose pulp, or, as the reaction of cellulose pulp to the hydroxyalkyl methyl cellulose proceeds, to partially reacted cellulose pulp, either before, after, or concurrently with the alkalizing agent added in the first stage. A single hydroxyalkylating agent or more than one, preferably only one, hydroxyalkylating agent may be utilized. The hydroxyalkylating agent is generally added in an amount of 0.2 to 2.0 mole of hydroxyalkylating agent per mole of anhydroglucose units. The hydroxyalkylating agent is advantageously added before heating the reaction mixture to the reaction temperature, i.e. at a temperature of from 30 to 70° C., preferably from 20 to 60° C.

An additional alkylating agent, different from a methylating agent, may also be added to the cellulose pulp, either before, after, or concurrently with the alkalizing agent added in the first stage. Non-limiting examples include ethyl chloride, ethyl bromide or ethyl iodide, diethyl sulphate and/or propyl chloride. The additional alkylating agent is generally added in an amount of 0.5 to 6 mole of alkylating agent per mole of anhydroglucose units. The alkylating agent is advantageously added before heating the reaction mixture to the reaction temperature, i.e. at a temperature of from 20 to 70° C., preferably from 40 to 60° C.

After accomplishment of the above described multistage etherification the obtained cellulose ether is typically further purified, dried and/or milled. Usually the cellulose ether is washed to remove salt and other reaction by-products. Any solvent in which the salt formed as a by-product of the etherification reaction is soluble may be employed, but water is usually utilized. The cellulose ether may be washed in the reactor, but is preferably washed in a separate washer located downstream of the reactor. Before or after washing, the cellulose ether may be stripped e.g. by exposure to steam to reduce the content of residual volatile organic compounds.

The cellulose ether can be dried to reduce moisture and the content of other volatile compounds to preferably 0.5 to 10.0 wt. %, more preferably 0.8 to 5.0 wt. % of water and other volatile compounds, based on the sum of the weight of the cellulose ether, water and other volatile compounds. Drying can be carried out using a conventional drier such as a tray drier, fluid bed drier, flash drier, agitation drier or tube drier. The reduced moisture and content of other volatile compounds enables the cellulose ether to be milled into particulate form. The dried cellulose ether can be milled to particulates of desired size by any suitable means known in the art such as a ball mill, an impact pulverizer, knife grinder or air-swept impact mill. If desired, drying and milling can be conducted simultaneously.

The cellulose ether is optionally subjected to a partial depolymerization process. Partial depolymerization processes are well known in the art and described, for example, in European Patent Applications EP 1,141,029; EP 210,917; EP 1,423,433; and U.S. Pat. No. 4,316,982. Alternatively, partial depolymerization can be achieved during the production of the cellulose ethers, for example by the presence of oxygen or an oxidizing agent. In such partial depolymerization process a cellulose ether can be obtained which has a viscosity of from 2.4 to 100 mPa·s, preferably from 2.5 to 50 mPa·s, and more preferably from 3 to 30 mPa·s, determined in a 2% by weight aqueous solution at 20° C. according to ASTM D2363-79 (Reapproved 2006).

The above-described cellulose ether can be used in combination with one or more polymers, preferably one or more water-soluble polymers, which are different from the above-described cellulose ether, such as one or more polysaccharides other than cellulose ethers which have anhydroglucose units joined by 1-4 linkages and which have methyl groups, hydroxyalkyl groups, and optionally alkyl groups being different from methyl as substituents; gelatins, poly(amino acids), such as poly(aspartic acid) or poly(glutamic acid); polylactic acid or a salt of such a polymerized acid or one or more synthetic polymers selected from the group consisting of polyalkylene oxides, such as ethylene oxide homo- and copolymers having a weight average molecular weight of at least 10,000, and homo- and copolymers comprising in polymerized form an unsaturated acid or a salt thereof, such as acrylic acid, methacrylic acid, or a salt thereof, an unsaturated amide, such as acrylamide; a vinyl ester, a vinylalcohol, an acetate, such as vinylacetate; an alkylene imine, such as ethylene imine; an oxyethylene alkylether, a vinylpyrrolidone, vinyloxazolidone, vinylmethyloxazolidone, ethylene sulfonic acid, a vinylamine, vinylpyridine, an ethylenically unsaturated sulfate or sulfonate or a combination of one or more of these polymers. A preferred type of water-soluble polymer is a polyethylene oxide, specifically homo- and copolymers of ethylene oxide. Ethylene oxide copolymers generally comprise at least 50 mole percent, preferably at least 70 mole percent, more preferably at least 85 mole percent ethylene oxide units. The most preferred ethylene oxide polymers are ethylene oxide homopolymers.

Preferably one or more of the above-described cellulose ethers wherein the ether substituents have a specific distribution pattern are the major portion of the polymers comprised in the melt-extruded polymer composition of the present invention. Typically one or more of the above-described cellulose ethers are from 55 to 100 percent, more preferably from 65 to 100 percent, most preferably from 85 to 100 percent, based on the total weight of the polymers.

A large variety of active ingredients can be included in the melt-extruded polymer composition of the present invention, preferably biologically active ingredients, particularly health-related biologically active ingredients, such as vitamins, herbals and mineral supplements, oral care ingredients and drugs, but also active ingredients not directly related to health, such as flavors, colors, taste masking compounds, cosmetically active ingredients, or ingredients active in agriculture. Cosmetic active ingredients may include breath freshening compounds like menthol, other flavors or fragrances, especially those used for oral hygiene, as well as actives used in dental and oral cleansing such as quaternary ammonium bases. The effect of flavors may be enhanced using flavor enhancers like tartaric acid, citric acid, vanillin, or the like. Examples of nutritional supplements usable in the invention include, but are not limited to, plant extracts, like cherry extract, Ginseng extract, tomato extract or berry extracts; glucosamine sulfate, chromium picolinate, Milk thistle extract, Grape seed extract, Ma Huang extract, Co-enzyme Q10, water soluble vitamins such as vitamin C niacin, vitamin B1 and vitamin B12, and fat soluble vitamins such as vitamins A, D, E, and K, minerals such as calcium, magnesium and zinc, among others.

It is not necessary for the active ingredient to be soluble in any given component of the composition. The active ingredient may be dissolved, partially dissolved or suspended in the polymer matrix of the composition. The active ingredient should generally be stable during the melt extrusion process conditions used. By stable, it is meant that a significant portion of the active ingredient will not be significantly degraded or decomposed throughout the melt extrusion process.

The melt-extruded polymer composition of the present invention forms a solid dispersion of one or more active ingredients a) as described above in at least one cellulose ether b) as described above. By melt-extrusion preferably a solid amorphous dispersion is produced wherein at least the major portion, more preferably at least 90 wt %, most preferably 100% of the active ingredient is in amorphous form and dispersed in the cellulose ether. The term "amorphous" as used herein means that the active ingredient does not have a long-range three-dimensional translational order. The solid dispersion is substantially more homogeneous than a simple blend of the active ingredient(s) a) and the cellulose ether(s) b). As discussed further above, skilled artisans have made the general suggestion that solid dispersions can be utilized as a strategy to increase the bioavailability of poorly soluble drugs by improving their rate and extent of dissolution.

It has been found that the above-described cellulose ethers, wherein the ether substituents have a specific distribution pattern, are able to maintain the concentration of poorly water-soluble active ingredients, such as poorly water-soluble drugs, in aqueous solutions at supersaturation levels. A considerably higher concentration of a poorly water-soluble active ingredient in an aqueous solution can be maintained than in the absence of an esterified cellulose ether described above. The degree of supersaturation of a poorly water-soluble active ingredient in an aqueous solution depends on various factors, such as the physical stability and the dissolution rate of a given active ingredient. Dwayne T. Friesen et al. in MOLECULAR PHARMACEUTICS VOL. 5, NO. 6, 1003-1019, 2008 have classified compounds with a structurally diverse range of physicochemical properties on a physical property map Tm/Tg ratio versus log P. The log P value is a standard measure of the lipophilicity of a compound. Log P, defined as the base 10 logarithm of the ratio of (1) the drug concentration in an octanol phase to (2) the drug concentration in a water phase when the two phases are in equilibrium with each other, is a widely accepted measure of hydrophobicity. Log P may be measured experimentally or calculated using methods known in the art. When using a calculated value for Log P, the highest value calculated using any generally accepted method for calculating Log P is used. Calculated Log P values are often referred to by the calculation method, such as C log P, A log P, and M log P. The Log P may also be estimated using fragmentation methods, such as Crippen's fragmentation method (27 J. Chem. lnf. Comput. Sci. 2 1 (1987)); Viswanadhan's fragmentation method (29 J. Chem. lnf. Comput. Sci. 163 (1989)); or Broto's fragmentation method (19 Eur. J. Med. Chem.-Chim Theor. 7 1 (1984)).

$$\log P_{oct/wat} = \log\left(\frac{[\text{solute}]_{octanol}}{[\text{solute}]_{water}^{un-ionized}}\right)$$

Compounds with high log P values are very hydrophobic and tend to have extremely low water solubilities (often less than 1 µg/mL when their melting points are above about 100° C.) and low propensities for wetting when placed into water.

Tm is the melting temperature and Tg is the glass transition temperature of the compound at atmospheric pressure. Dwayne T. Friesen et al. have divided the compounds into four groups based on their position on this physical property map Tm/Tg ratio versus log P (FIG. 14 on page 1018 in MOLECULAR PHARMACEUTICS VOL. 5, NO. 6, 2008). The first group, Group 1, consists of compounds with relatively low Tm/Tg ratios (<1.25 K/K) and low to moderate log P values (less than about 6); Compounds in Group 2 have somewhat higher Tm/Tg ratios (1.25–1.4) and low to moderate log P values (less than about 6). Compounds in Group 3 have even higher Tm/Tg values (greater than 1.4) and low to moderate log P values (less than about 6). Finally, Group 4 compounds have high log P values (at least about 6).

A preferred aspect of the present invention is a melt-extruded polymer composition which comprises at least one esterified cellulose ether as described above and additionally at least one active ingredient that has a Tm/Tg ratio of more than 1.0 up to 1.8, preferably more than 1.1 up to 1.6, more preferably 1.15 up to 1.5, most preferably 1.25 to 1.40, wherein the melting temperature Tm and the glass transition temperature Tg each are in Kelvin. The active ingredient preferably has a log P of more than 1 up to 11, preferably 1.5 to 8, most preferably 2 to 6.

The active ingredient does not need to be a low-solubility active ingredient in order to benefit from this invention, although low-solubility active ingredients represent a preferred class for use with the invention. An active ingredient that exhibits appreciable aqueous solubility in the desired environment of use may have an aqueous solubility up to 1 to 2 mg/mL, or even as high as 20 to 40 mg/mL. Useful low-solubility drugs are listed in the International Patent Application WO 2005/115330, pages 17-22.

The melt-extruded polymer composition of the present invention may comprise one or more optional additives c), such as one or more fillers, pigments, colorants, lubricants, plasticizers, stabilizers such as antioxidants, slip agents and anti-block agents. Although the polymer composition utilized for producing the melt-extruded polymer composition of the present invention need not contain a plasticizer to render it hot-melt extrudable, a plasticizer may be included as an additional component. The plasticizer should be able to lower the glass transition temperature or softening point of the active composition in order to allow for lower processing temperature, extruder torque and pressure during the hot-melt extrusion process. Plasticizers also generally reduce the viscosity of a polymer melt thereby allowing for lower processing temperature and extruder torque during hot-melt extrusion. Useful plasticizers are, for example, low molecular weight polyalcohols, such as ethylene glycol, propylene glycol, 1,2 butylene glycol, 2,3-butylene glycol, polyethylene glycols such as diethylene glycol, triethylene glycol, tetraethylene glycol, other polyethylene glycols having a molecular weight lower than 1000 g/mol or polypropylene glycols having a molecular weight lower than 2000 g/mol, cetanol, triglycerides, polyoxyethylene-polyoxypropylene glycol (Pluronic), triacetin or triethyl citrate. However, one advantage of the present invention is that the amount of one or more lubricants or plasticizers or stabilizers in the polymer composition to be melt-extruded can be reduced or even avoided when preparing the melt-extruded polymer composition of the present invention. Depending on its structure, the active ingredient may function as a plasticizer.

The melt-extruded polymer composition of the present invention preferably comprises from 20 to 99.9 percent, more preferably from 30 to 98 percent, and most preferably from 60 to 95 percent of a cellulose ether a) as described above, and preferably from 0.1 to 80 percent, more preferably from 2 to 70 percent, and most preferably from 5 to 40 percent of an active ingredient b), based on the total weight of the cellulose ether a) and the active ingredient b). The combined amount of the cellulose ether a) and the active ingredient b) is preferably at least 70 percent, more preferably at least 80 percent, and most preferably at least 90 percent, based on the total weight of the melt-extruded polymer composition. The remaining amount, if any, are one or more of the adjuvants c) as described above. The melt-extruded polymer composition can comprise one or more of the cellulose ethers a), one or more of the active ingredients b), and optionally one or more of the adjuvants c), however their total amount is generally within the above-mentioned ranges.

The process for producing a melt-extruded composition comprises the steps of i) blending a) at least one cellulose ether defined above, b) one or more active ingredients and c) one or more optional additives, and ii) subjecting the blend to melt-extrusion. The term "melt extrusion" as used herein includes processes known as injection molding, melt casting and compression molding. Techniques for melt-extruding compositions comprising an active ingredient such as a drug are known and described by Joerg Breitenbach, Melt extrusion: from process to drug delivery technology, *European Journal of Pharmaceutics and Biopharmaceutics* 54 (2002) 107-117 or in European Patent Application EP 0 872 233.

The blends of a), b) and optionally c) described herein are generally melt-extrudable. As used herein, the term "melt-extrudable" refers to a compound or composition that may be melt-extruded, particularly hot-melt extruded. A hot-melt extrudable polymer composition is one that is sufficiently rigid at 25° C. and atmospheric pressure, when it is not in particulate form such as a powder or granules, but is capable of deformation or forming a semi-liquid state under elevated heat or pressure, that means at a temperature above 25° C. or a pressure above atmospheric pressure. The above-mentioned components a), b) and optionally c) are preferably mixed in the form of particles, more preferably in powdered form. The components a), b) and optionally c) may be pre-mixed before feeding the blend into a device utilized for melt-extrusion. Useful devices for melt-extrusion, specifically useful extruders, are known in the art. Alternatively, the components a), b) and optionally c) may be fed separately into the extruder and blended in the device before or during a heating step. Preferably components a), b) and optionally c) are pre-blended in an extruder hopper and fed from there into the extruder. Although in some embodiments of the invention the mixture or the components to be mixed in the extruder may contain liquid materials, dry feed is advantageously employed in the melt-extrusion process of the present invention. The composition or the components that has or have been fed into an extruder are passed through a heated area of the extruder at a temperature which will melt or soften the composition or at least one or more components thereof to form a blend throughout which the active ingredient is dispersed. The blend is subjected to melt-extrusion and caused to exit the extruder. Typical extrusion melt temperatures are from 50 to 210° C., preferably from 70 to 200° C., more preferably from 90 to 190° C., as determined by the setting for the extruder heating zone(s). An operating temperature range should be selected that will minimize the degradation or decomposition of the active ingredient and other components of the composition during processing. The extruder used to practice the invention preferably is a commercially available model equipped to handle dry feed and having a solid conveying zone, one or multiple heating zones, and an extrusion die. It is particularly advantageous for the extruder to possess multiple separate temperature controllable heating zones. Single or multiple screw extruders, preferably twin screw extruders, can be used in the melt-extrusion process of the present invention.

The molten or softened mixture obtained in the extruder are forced through one or more exit openings, such as one or more nozzles or dies. The openings can have any shape known in the art, such as for example square, rectangular, circular or annular. The molten or softened mixture then exits via a die or other such element having one or a plurality of openings, at which time, the melt-extruded blend (now called the extrudate) begins to harden. Since the extrudate is still warm or hot upon exiting the die, it may be easily shaped, molded, chopped, ground, spheronized into beads, cut into strands, tableted or otherwise processed to the desired physical form.

One embodiment of the process of the present invention for producing a melt-extruded polymer composition comprises the step of subjecting the blend to melt-extrusion to produce a film. According to this embodiment the extrudate is molded, preferably drawn, to a film of the desired thickness. Preferably a film in the form of a melt-extruded mono-layer film is produced. The melt-extruded polymer composition can be used in the form of a film. Alternatively, the melt-extruded film can be cut into pieces in a known manner to produce dosage forms.

If a multi-layer film is to be produced, the melt-extruded film can be combined with one or more other films layers during or after melt-extrusion to produce a multi-layer film.

The melt-extruded film can be combined with one or more other films layers while it is still warm or hot or after it has been cooled down. Alternatively, a melt-extruded multi-layer film can be produced via coextrusion, wherein one or more of the layers are produced from the polymer composition comprising the above-mentioned components a), b) and optionally c). The multi-layer film can be cut into pieces in a known manner to produce dosage forms.

Another embodiment of the process of the present invention for producing a melt-extruded polymer composition comprises the steps of subjecting the blend to melt-extrusion to produce strands and comminuting the melt-extruded strands to beads, pellets, granules, tablets or a powder.

The melt-extruded polymer composition of the present invention in powder form can be optionally blended with adjuvants and can be used for producing dosage forms, such as tablets, pills, granules, pellets, caplets, microparticles, fillings of capsules, or into pastes, creams, suspensions or slurries.

Another embodiment of the process of the present invention for producing a melt-extruded polymer composition comprises the steps of subjecting the blend to melt-extrusion and contacting the melt-extruded blend with pins to manufacture capsules, preferably injection-molded capsules. A preferred method is the "cold-pin method". In this method the melt-extruded polymer composition comprising a) at least one cellulose ether defined above, b) one or more active ingredients and c) one or more optional additives, such as a gelling agent like carrageenan, pectin, gellan gum, or another sequestering agent or gelling aid, such as potassium, magnesium, ammonium, or calcium ions is contacted with cold pins. In the cold-pin method pins are generally kept at room temperature and are dipped into the molten or at least softened melt-extruded polymer composition. A film is obtained on the dipping pins, and the film is cooled on the dipping pins to obtain molded capsule shells on the pins.

The present invention is further illustrated by the following examples which are not to be construed to limit the scope of the invention. Unless otherwise mentioned, all parts and percentages are by weight.

EXAMPLES

The determination of the % methoxyl and % hydroxypropoxyl in hydroxypropyl methylcellulose (HPMC) is carried out according to the United States Pharmacopeia (USP 32). The values obtained are % methoxyl and % hydroxypropoxyl. These are subsequently converted into degree of substitution (DS) for methyl substituents and molar substitution (MS) for hydroxypropyl substituents. Residual amounts of salt have been taken into account in the conversion.

The viscosity of the HPMC is measured as a 2% by weight aqueous solution at 20° C. according to ASTM D2363-79 (Reapproved 2006).
Determination of s23/s26

The determination of ether substituents in cellulose ethers is generally known and e.g., described in Carbohydrate Research, 176 (1988) 137–144, Elsevier Science Publishers B. V., Amsterdam, DISTRIBUTION OF SUBSTITUENTS IN O-ETHYL-O-(2-HYDROXYETHYL)CELLULOSE by Bengt Lindberg, Ulf Lindquist, and Olle Stenberg.

Specifically, determination of s23/s26 is conducted as follows: 10–12 mg of the cellulose ether are dissolved in 4.0 mL of dry analytical grade dimethyl sulfoxide (DMSO) (Merck, Darmstadt, Germany, stored over 0.3 nm molecular sieve beads) at about 90° C. under stirring and then cooled down to room temperature again. The solution is left stirring at room temperature over night to ensure complete solubilization. The entire reaction including the solubilization of the cellulose ether is performed using a dry nitrogen atmosphere in a 4 mL screw cap vial. After solubilization the dissolved cellulose ether is transferred to a 22 mL screw cap vial. Powdered sodium hydroxide (freshly pestled, analytical grade, Merck, Darmstadt, Germany) and ethyl iodide (for synthesis, stabilized with silver, Merck-Schuchardt, Hohenbrunn, Germany) in a thirty fold molar excess of the reagents sodium hydroxide and ethyl iodide per hydroxyl group of the anhydroglucose unit are added and the solution is vigorously stirred under nitrogen in the dark for three days at ambient temperature. The perethylation is repeated with addition of the threefold amount of the reagents sodium hydroxide and ethyl iodide compared to the first reagent addition and further stirring at room temperature for additional two days. Optionally the reaction mixture can be diluted with up to 1.5 mL DMSO to ensure good mixing during the course of the reaction. 5 mL of 5% aqueous sodium thiosulfate solution is poured into the reaction mixture and the obtained solution is then extracted three times with 4 mL of dichloromethane. The combined extracts are washed three times with 2 mL of water. The organic phase is dried with anhydrous sodium sulfate (ca. 1 g). After filtration the solvent is removed in a gentle stream of nitrogen and the sample is stored at 4° C. until further sample preparation.

Hydrolysis of about 5 mg of the perethylated samples is performed under nitrogen in a 2 mL screw cap vial with 1 mL of 90% aqueous formic acid under stirring at 100° C. for 1 hour. The acid is removed in a stream of nitrogen at 35-40° C. and the hydrolysis is repeated with 1 mL of 2M aqueous trifluoroacetic acid for 3 hours at 120° C. in an inert nitrogen atmosphere under stirring. After completion the acid is removed to dryness in a stream of nitrogen at ambient temperature using ca. 1 mL of toluene for co-distillation.

The residues of the hydrolysis are reduced with 0.5 mL of 0.5 M sodium borodeuteride in 2N aqueous ammonia solution (freshly prepared) for 3 hours at room temperature under stirring. The excess reagent is destroyed by drop wise addition of ca. 200 µL of concentrated acetic acid. The resulting solution is evaporated to dryness in a stream of nitrogen at ca. 35-40° C. and subsequently dried in vacuum for 15 min at room temperature. The viscous residue is dissolved in 0.5 mL of 15% acetic acid in methanol and evaporated to dryness at room temperature. This is done five times and repeated four times with pure methanol. After the final evaporation the sample is dried in vacuum overnight at room temperature.

The residue of the reduction is acetylated with 600 µL of acetic anhydride and 150 µL of pyridine for 3 hrs at 90° C. After cooling the sample vial is filled with toluene and evaporated to dryness in a stream of nitrogen at room temperature. The residue is dissolved in 4 mL of dichloromethane and poured into 2 mL of water and extracted with 2 mL of dichloromethane. The extraction is repeated three times. The combined extracts are washed three times with 4 mL of water and dried with anhydrous sodium sulfate. The dried dichloromethane extract is subsequently submitted to GC analysis. Depending on the sensitivity of the GC system, a further dilution of the extract can be necessary.

Gas-liquid (GLC) chromatographic analyses are performed with Hewlett Packard 5890A and 5890A Series II type of gas chromatographs equipped with J&W capillary columns DB5, 30 m, 0.25 mm ID, 0.25 µm phase layer thickness operated with 1.5 bar helium carrier gas. The gas chromatograph is programmed with a temperature profile that holds constant at 60° C. for 1 min, heats up at a rate of 20° C./min to 200° C., heats further up with a rate of 4° C./min to 250° C., heats further up with a rate of 20° C./min to 310° C. where it is held constant for another 10 min. The injector temperature is set to 280° C. and the temperature of the flame ionization detector (FID) is set to 300° C. 1 µL of the samples is injected in the splitless mode at 0.5 min valve time. Data are acquired and processed with a LabSystems Atlas work station.

Quantitative monomer composition data are obtained from the peak areas measured by GLC with FID detection. Molar responses of the monomers are calculated in line with the effective carbon number (ECN) concept but modified as described in the table below. The effective carbon number (ECN) concept has been described by Ackman (R. G. Ackman, J. Gas Chromatogr., 2 (1964) 173-179 and R. F. Addison, R. G. Ackman, J. Gas Chromatogr., 6 (1968) 135-138) and applied to the quantitative analysis of partially alkylated alditol acetates by Sweet et. al (D. P. Sweet, R. H. Shapiro, P. Albersheim, Carbohyd. Res., 40 (1975) 217–225).

ECN Increments Used for ECN Calculations:

| Type of carbon atom | ECN increment |
|---|---|
| hydrocarbon | 100 |
| primary alcohol | 55 |
| secondary alcohol | 45 |

In order to correct for the different molar responses of the monomers, the peak areas are multiplied by molar response factors MRFmonomer which are defined as the response relative to the 2,3,6-Me monomer. The 2,3,6-Me monomer is chosen as reference since it is present in all samples analyzed in the determination of s23/s26.

MRFmonomer=ECN2,3,6-Me/ECNmonomer

The mole fractions of the monomers are calculated by dividing the corrected peak areas by the total corrected peak area according to the following formulas:

$$s23=[(23\text{-}Me+23\text{-}Me\text{-}6\text{-}HAMe+23\text{-}Me\text{-}6\text{-}HA+23\text{-}Me\text{-}6\text{-}HAHAMe+23\text{-}Me\text{-}6\text{-}HAHA]; \text{ and}$$

$$s26=[(26\text{-}Me+26\text{-}Me\text{-}3\text{-}HAMe+26\text{-}Me\text{-}3\text{-}HA+26\text{-}Me\text{-}3\text{-}HAHAMe+26\text{-}Me\text{-}3\text{-}HAHA], \text{ wherein}$$

s23 is the sum of the molar fractions of anhydroglucose units which meet the following conditions:
a) the two hydroxy groups in the 2- and 3-positions of the anhydroglucose unit are substituted with methyl groups and the 6-position is not substituted (=23-Me);
b) the two hydroxy groups in the 2- and 3-positions of the anhydroglucose unit are substituted with methyl groups and the 6-position is substituted with methylated hydroxyalkyl (=23-Me-6-HAMe) or with a methylated side chain comprising 2 hydroxyalkyl groups (=23-Me-6-HAHAMe); and
c) the two hydroxy groups in the 2- and 3-positions of the anhydroglucose unit are substituted with methyl groups and the 6-position is substituted with hydroxyalkyl (=23-Me-6-HA) or with a side chain comprising 2 hydroxyalkyl groups (=23-Me-6-HAHA). s26 is the sum of the molar fractions of anhydroglucose units which meet the following conditions:
a) the two hydroxy groups in the 2- and 6-positions of the anhydroglucose unit are substituted with methyl groups and the 3-position is not substituted (=26-Me);
b) the two hydroxy groups in the 2- and 6-positions of the anhydroglucose unit are substituted with methyl groups and the 3-position is substituted with methylated hydroxyalkyl (=26-Me-3-HAMe) or with a methylated side chain comprising 2 hydroxyalkyl groups (=26-Me-3-HAHAMe); and
c) the two hydroxy groups in the 2- and 6-positions of the anhydroglucose unit are substituted with methyl groups and the 3-position is substituted with hydroxyalkyl (=26-Me-3-HA) or with a side chain comprising 2 hydroxyalkyl groups (=26-Me-3-HAHA).

The results of the determination of the substituents in the HAMC are listed in Table 4 below. In the case of HPMC's hydroxyalkyl (HA) is hydroxypropyl (HP) and methylated hydroxyalkyl (HAMe) is methylated hydroxypropyl (HPMe).

Example 1

Hydroxypropyl methylcellulose (HPMC) was produced according to the following procedure. Finely ground wood cellulose pulp was loaded into a jacketed, agitated reactor. The reactor was evacuated and purged with nitrogen to remove oxygen and then evacuated again. The reaction was carried out in two stages. In the first stage a 50 weight percent aqueous solution of sodium hydroxide was sprayed onto the cellulose in an amount of 3.0 mole of sodium hydroxide per mole of anhydroglucose units in the cellulose and the temperature was adjusted to 40° C. After stiffing the mixture of aqueous sodium hydroxide solution and cellulose for about 30 minutes at 40° C., 1.5 mole of dimethyl ether, 5.0 mole of methyl chloride and 1.6 mole of propylene oxide per mole of anhydroglucose units were added to the reactor. The contents of the reactor were then heated in 60 min to 80° C. After having reached 80° C., the first stage reaction was allowed to proceed for 25 min Then the reaction was cooled down to 60° C. within 20 min. Then a 50 weight percent aqueous solution of sodium hydroxide at an amount of 1.00 mole of sodium hydroxide per mole of anhydroglucose units was added over a time period of 60 min. The rate of addition was 0.017 mole of sodium hydroxide per mole of anhydroglucose units per minute. After the second stage addition was completed, the contents of the reactor were heated up to 80° C. within 20 min and then kept at a temperature of 80° C. for 120 min After the reaction the reactor was vented and cooled down to about 50° C. The contents of the reactor were removed and transferred to a tank containing hot water. The crude HPMC was then neutralized with formic acid and washed chloride free with hot water (assessed by $AgNO_3$ flocculation test), cooled to room temperature and dried at 55° C. in an air-swept drier. The material was then ground using an Alpine UPZ mill using a 0.5 mm screen.

The obtained powder was partially depolymerized in a known manner by heating the powderous samples with up to 3.0 g gaseous hydrogen chloride per kg of powder at a temperature of at most 85° C. until the desired viscosity was achieved. The partially depolymerized hydroxypropyl methylcellulose was neutralized with sodium bicarbonate.

Example 2

Example 1 was repeated, except that the amount of propylene oxide added to the reaction mixture was 1.0 mole of propylene oxide per mole of anhydroglucose units.

The obtained powder was partially depolymerized in a known manner by heating the powderous samples with up to 3.0 g gaseous hydrogen chloride per kg of powder at a temperature of at most 85° C. until the desired viscosity was achieved. The partially depolymerized hydroxypropyl methylcellulose was neutralized with sodium bicarbonate.

Comparative Example A

The hydroxypropyl methyl cellulose of Comparative Example A was produced according to the following procedure. Finely ground wood cellulose pulp was loaded into a jacketed, agitated reactor. The reactor was evacuated and purged with nitrogen to remove oxygen and then evacuated again. The reaction was carried out in one stage. A 50 weight percent aqueous solution of sodium hydroxide was sprayed onto the cellulose in an amount of 3.90 mole of sodium hydroxide per mole of anhydroglucose units in the cellulose and the temperature was adjusted to 40° C. After stiffing the mixture of aqueous sodium hydroxide solution and cellulose for about 20 minutes at 40° C., 2.07 mole of dimethyl ether, 4.40 mole of methyl chloride and 1.00 mole of propylene oxide per mole of anhydroglucose units were added to the reactor. The contents of the reactor were then heated in 80 min to 80° C. After having reached 80° C., the first stage reaction was allowed to proceed for 60 min After the reaction the reactor was vented and cooled down to about 50° C. The contents of the reactor were removed and further processed as described in Example 1.

The obtained powder was partially depolymerized in a known manner by heating the powderous samples with up to 3.0 g gaseous hydrogen chloride per kg of powder at a temperature of at most 85° C. until the desired viscosity was achieved. The partially depolymerized hydroxypropyl methylcellulose was neutralized with sodium bicarbonate.

The properties of the hydroxypropyl methyl celluloses (HPMC) of Examples 1 to 2 and of Comparative Example A are listed in Table 2 below. Details on the s23/s26 determination are listed in Table 1 below.

samples of each blend were weighed into aluminium pans and hermetically sealed. Differential Scanning calorimetry (DSC) experiments were conducted in the modulated mode with a modulation frequency of +/−1° C./min Samples were equilibrated at 25° C. for 5 minutes before raising the temperature from 25° C. to 250° C. at a rate of 5° C./min. The temperature which was recorded at the peak of the melting endotherm, observed in the total heat flow signal, was taken as the melting point for ketoprofen in the physical blend with HPMC. This temperature was compared against the melting point for pure ketoprofen, similarly measured, to obtain the melting point depression.

Extrusion

Extrusion products were generated using a Haake MiniLab II micro compounder utilizing twin co-rotating conical intermeshing advancing flight screws. The unit employed was driven by a 400 W drive motor, had a maximum screw speed of 360 rpm, and was comprised of a single heating zone with a recirculation chamber. The exit port comprised a 2 mm strand die and the produced materials were collected as single strands. Table 3 summarizes the conditions used for the extrusion. Table 4 summarizes the results of the extrusion.

TABLE 3

| Cellulose Ether Example | Cellulose ether [wt. %]* | Active ingredient [wt. %]* | Extrusion temp. [° C.] | Batch Size [g] | Screw speed [rpm] | Torque [Nm] | Die pressure [kPa] |
|---|---|---|---|---|---|---|---|
| 1 | 60 | 40 | 120 | 6.5 | 60 | 50 | 58 |
| 2 | 60 | 40 | 120 | 6.5 | 60 | 82 | 90 |
| A | 60 | 40 | 120 | 6.5 | 60 | 24 | 35 |

*Based on total weight of composition to be melt-extruded

TABLE 1

| | (Comparative) Example | | |
|---|---|---|---|
| | 1 | 2 | A |
| DS (USP) | 1.93 | 1.92 | 1.83 |
| MS (USP) | 0.35 | 0.2 | 0.19 |
| mol fraction (26-Me) | 0.2452 | 0.2621 | 0.2236 |
| mol fraction (26-Me-3-HA) | 0.0201 | 0.0145 | 0.0162 |
| mol fraction (26-Me-3-HAHA) | 0.0000 | 0.0000 | 0.0000 |
| mol fraction (26-Me-3HAMe) | 0.0031 | 0.0021 | 0.0026 |
| mol fraction (26-Me-3HAHAMe) | 0.0000 | 0.0000 | 0.0000 |
| mol fraction (23-Me) | 0.0697 | 0.0748 | 0.0933 |
| mol fraction (23-Me-6-HA) | 0.0158 | 0.0109 | 0.0109 |
| mol fraction (23-Me-6-HAHA) | 0.0000 | 0.0000 | 0.0000 |
| mol fraction (23-Me-6-HAMe) | 0.0000 | 0.0000 | 0.0000 |
| mol fraction (23-Me-6-HAHAMe) | 0.0000 | 0.0000 | 0.0000 |
| s23/s26 | 0.32 | 0.31 | 0.43 |
| s23/s26 − 0.2 * MS | 0.25 | 0.27 | 0.39 |

TABLE 4

| Cellulose Ether Example | Extrudate quality | Glass transition temp. (Tg) of Milled Extrudate | Amorphous Solid Dispersion Formed |
|---|---|---|---|
| 1 | Translucent, nearly colorless, flexible | 10.79 | Yes |
| 2 | Translucent, nearly colorless, flexible | 8.02 | Yes |
| A | Translucent, slightly browned, partially rigid | 8.55 | No |

Evaluation of Amorphous Solid Dispersion by Differential Scanning Calorimetry

Small (<5 mg) samples of each extrudate, that had been milled into a fine powder, were weighed into aluminium pans and hermetically sealed. Differential Scanning calorimetry (DSC) experiments were conducted in the modulated mode

TABLE 2

| (Comp.) Example | DS (methyl) | MS (hydroxy-propyl) | Viscosity at 20° C. [mPa · s] | s23/s26 | s23/s26 − 0.2 * MS (hydroxy-propyl) | Tm Depression of 60/40 HPMC/ Ketoprofen Physical Blend [° C.] |
|---|---|---|---|---|---|---|
| 1 | 1.93 | 0.35 | 4.1 | 0.32 | 0.25 | −5.37 |
| 2 | 1.92 | 0.20 | 4.4 | 0.31 | 0.27 | −2.7 |
| A | 1.83 | 0.19 | 3.1 | 0.43 | 0.39 | −12.25 |

Determination of Melting Point (Tm) Depression by Differential Scanning Calorimetry Blends of ketoprofen and HPMC (60/40 w/w) were prepared by physically mixing the materials. Small (<5 mg)

with a modulation frequency of +/−1° C./min Samples were equilibrated at −25° C. for 5 minutes before raising the temperature from −25° C. to 250° C. at a rate of 5° C./min. The reversing heat flow signal from each of the samples was examined for the presence of glass transitions and for evidence of a melt signal from crystalline ketoprofen. If no melt signal was observed, the system was considered to be amorphous.

Skilled artisans recognize the significant depression of the melting temperature Tm of the drug ketoprofen in comparative example A, where ketoprofen was blended with the HPMC, in comparison to the Tm of ketoprofen alone (see Table 2), as an indication of superior miscibility between the HPMC and drug and an early predictor of success for the formation of an amorphous solid dispersion. However, while the comparative example A demonstrated improved miscibility during the extrusion process (as evidenced by reduced torque), the comparative example A was not able to form an amorphous solid dispersion (see Table 4). Surprisingly, the inventive composition of cellulose ether and active ingredient was able to be extruded under reasonable torque and die pressure and produced an amorphous solid dispersion under identical formulation and processing conditions.

What is claimed is:

1. A melt-extruded polymer composition comprising a) at least one cellulose ether, b) one or more active ingredients and c) one or more optional additives, wherein said at least one cellulose ether has anhydroglucose units joined by 1-4 linkages and has methyl groups, hydroxyalkyl groups, and optionally alkyl groups being different from methyl as substituents such that
said at least one cellulose ether has an MS (hydroxyalkyl) of 0.05 to 0.55
and
hydroxyl groups of anhydroglucose units are substituted with methyl groups such that [s23/s26−0.2*MS(hydroxyalkyl)] is 0.28 or less,
wherein s23 is the molar fraction of anhydroglucose units wherein only the two hydroxyl groups in the 2- and 3-positions of the anhydroglucose unit are substituted with a methyl group and
wherein s26 is the molar fraction of anhydroglucose units wherein only the two hydroxyl groups in the 2- and 6-positions of the anhydroglucose unit are substituted with a methyl group.

2. The melt-extruded polymer composition of claim 1 wherein said at least one cellulose ether is a hydroxyalkyl methyl cellulose.

3. The melt-extruded polymer composition of claim 2 wherein said at least one cellulose ether is a hydroxypropyl methyl cellulose.

4. The melt-extruded polymer composition of claim 1 wherein said at least one cellulose ether has an [s23/s26−0.2*MS(hydroxyalkyl)] of 0.25 or less.

5. The melt-extruded polymer composition of claim 1 wherein said at least one cellulose ether has a DS(methyl) of 1.2 to 2.2.

6. The melt-extruded polymer composition of claim 1 comprising from 20 to 99.9 percent of at least one cellulose ether a) and from 0.1 to 80 percent of one or more active ingredients b), based on the total weight of a) and b).

7. The melt-extruded polymer composition of claim 1 which optionally comprises further comprises one or more polymers which are different from said at least one cellulose ether a) such that the amount of said at least one cellulose ether a) is from at least 55 to 100 percent, based on the total weight of the polymers.

8. The melt-extruded polymer composition of claim 1 wherein the combined amounts of said at least one cellulose ether a) and said one or more active ingredients b) are at least 70 percent, based on the total weight of the polymer composition.

9. The melt-extruded polymer composition of claim 1 in the form of strands, pellets, granules, pills, tablets, caplets, microparticles, fillings of capsules or injection molded capsules or in the form of a powder, film, paste, cream, suspension or slurry.

10. A process for producing a melt-extruded polymer composition comprising the steps of
i) blending a) at least one cellulose ether, b) one or more active ingredients and c) one or more optional additives, and
ii) subjecting the blend to melt-extrusion,
wherein said at least one cellulose ether has anhydroglucose units joined by 1-4 linkages and has methyl groups, hydroxyalkyl groups, and optionally alkyl groups being different from methyl as substituents such that
said at least one cellulose ether has an MS (hydroxyalkyl) of 0.05 to 0.55
and
hydroxyl groups of anhydroglucose units are substituted with methyl groups such that [s23/s26−0.2*MS(hydroxyalkyl)] is 0.28 or less,
wherein s23 is the molar fraction of anhydroglucose units wherein only the two hydroxyl groups in the 2- and 3-positions of the anhydroglucose unit are substituted with a methyl group and
wherein s26 is the molar fraction of anhydroglucose units wherein only the two hydroxyl groups in the 2- and 6-positions of the anhydroglucose unit are substituted with a methyl group.

11. The process of claim 10, further comprising the step of (iii) subjecting the melt-extruded blend to shaping, molding, chopping, grinding, spheronizing into beads, cutting into strands, or tableting.

12. The process of claim 10 comprising the steps of subjecting the blend to melt-extrusion to produce strands and comminuting the melt-extruded strands to beads, pellets, granules, tablets or a powder.

13. The process of claim 10 comprising the step of subjecting the blend to melt-extrusion to produce a film and comprising the optional steps of
I) cutting the melt-extruded film into pieces, or
II) combining the melt-extruded film with one or more other films during or after melt-extrusion to produce a multi-layer film, with or without subsequently cutting the film into pieces.

14. The process of claim 10 comprising the steps of subjecting the blend to melt-extrusion and contacting the melt-extruded blend with pins to manufacture capsules.

15. The melt-extruded polymer composition of claim 4 wherein said at least one cellulose ether is a hydroxypropyl methyl cellulose and has a DS(methyl) of 1.2 to 2.2.

16. The melt-extruded polymer composition of claim 1 wherein said at least one cellulose ether a) makes up about 100 percent of the total weight of the polymers in the composition.

* * * * *